(12) United States Patent
Horvath et al.

(10) Patent No.: US 6,235,792 B1
(45) Date of Patent: May 22, 2001

(54) PHOSPHATE SALT OF ISOPROPYL-METHYL-[2-(3-N-PROPOXYPHENOXY)ETHYL]AMINE

(75) Inventors: Karol Horvath, Södertälje; Ulf Larsson, Åkers Styckebruk; Rune Sandberg, Leksand, all of (SE)

(73) Assignee: Astra AB, Sodertalje (SE)

( * ) Notice: Subject to any disclaimer, the term of this patent is extended or adjusted under 35 U.S.C. 154(b) by 0 days.

(21) Appl. No.: 09/254,420

(22) PCT Filed: Dec. 15, 1998

(86) PCT No.: PCT/SE98/02316

§ 371 Date: Mar. 8, 1999

§ 102(e) Date: Mar. 8, 1999

(87) PCT Pub. No.: WO99/32431

PCT Pub. Date: Jul. 1, 1999

(30) Foreign Application Priority Data

Dec. 22, 1997 (SE) .................................................. 9704835

(51) Int. Cl.⁷ .................................................... A61K 31/135
(52) U.S. Cl. .............................................. 514/651; 564/354
(58) Field of Search .............................. 564/354; 514/651

(56) References Cited

U.S. PATENT DOCUMENTS 3,105,854  10/1963  Druey et al. ........................ 260/570.7

FOREIGN PATENT DOCUMENTS

WO 97/15548  5/1997  (WO) .......................... C07C/217/20

*Primary Examiner*—Samuel Barts
(74) *Attorney, Agent, or Firm*—Michael A. Sanzo; Pillsbury Madison & Sutro LLP

(57) ABSTRACT

The present invention relates to a novel monophosphate salt of isopropyl-methyl-[2-(3-n-propoxyphenoxy)ethyl]amine. Moreover, the present invention also relates to a process for the preparation of the monophosphate salt of isopropyl-methyl-[2-(3-n-propoxyphenoxy)ethyl]amine as well as a pharmaceutical formulation containing it and its use in medicine.

17 Claims, No Drawings

PHOSPHATE SALT OF ISOPROPYL-METHYL-[2-(3-N-PROPOXYPHENOXY) ETHYL]AMINE

CROSS REFERENCE TO RELATED APPLICATIONS

The present application represents U.S. national stage of international application PCT/SE98/02316 with an international filing date of Dec. 15, 1998. The international application claims priority to Swedish application 9704835-9, filed on Dec. 22, 1997.

FIELD OF THE INVENTION

The present invention relates to a novel phosphate salt of isopropyl-methyl-[2-(3-n-propoxyphenoxy)ethyl]amine. Additionally, the present invention also relates to a process for the preparation of a phosphate salt of isopropyl-methyl-[2-(3-n-propoxyphenoxy)ethyl]amine as well as a pharmaceutical formulation containing it and its use in medicine.

BACKGROUND OF THE INVENTION AND PRIOR ART

Isopropyl-methyl-[2-(3-n-propoxyphenoxy)ethyl]amine is a compound with anaesthetic properties. It is therefore useful as an anaesthetic compound for the treatment of pain, including localised pain.

WO 9715548 discloses isopropyl-methyl-[2-(3-n-propoxyphenoxy)ethyl]amine as well as a process for its preparation. Said process comprises a couple of reaction steps starting with reacting 3-n-propoxyphenol with 1,2-dibromoethane resulting in 1-(2-bromoethoxy)-3-n-propoxybenzene. Further, 1-(2-bromoethoxy)-3-n-propoxybenzene is reacted with N-methylisopropylamine in an autoclave. The product, isopropyl-methyl-[2-(3-n-propoxyphenoxy)ethyl]amine, was thereafter further purified by distillation in vacua.

SUMMARY OF THE INVENTION

The object of the present invention is to provide a monophosphate salt of isopropyl-methyl-[2-(3-n-propoxyphenoxy)ethyl)]amine.

According to the invention there is also provided a process for the preparation of the monophosphate salt of isopropyl-methyl-[2-(3-n-propoxyphenoxy)ethyl]amine which comprises treating isopropyl-methyl-[2-(3-n-propoxyphenoxy)ethyl]amine with phosphoric acid in a solvent system.

The monophosphate salt of isopropyl-methyl-[2-(3-n-propoxyphenoxy)ethyl]amine is a crystalline and stable salt of isopropyl-methyl-[2-(3-n-propoxyphenoxy)ethyl]amine and therefore has advantageous properties.

Additionally, the crystalline monophosphate salt of isopropyl-methyl-[2-(3-n-propoxyphenoxy)ethyl]amine can be used to introduce a crystalline intermediate in the process for the preparation of isopropyl-methyl-[2-(3-n-propoxyphenoxy)ethyl]amine. This introduces a simple and convenient purification step in a reaction sequence where all other intermediates are syrups. Thereby, the time and energy consuming distillation used in processes according to prior art is avoided. The crystallization of the monophosphate salt of isopropyl-methyl-[2-(3-n-propoxyphenoxy)ethyl]amine results in an intermediate of a high purity that can be further converted to the corresponding isopropyl-methyl-[2-(3-n-propoxyphenoxy)ethyl]amine by a simple alkalization step.

PREPARATION

In the preparation of the monophosphate salt of isopropyl-methyl-[2-(3-n-propoxyphenoxy)ethyl]amine the content of isopropyl-methyl-[2-(3-n-propoxyphenoxyethyl]amine in ethyl acetate is first assayed and adjusted to 6–10 ml ethyl acetate per gram of isopropyl-methyl-[2-(3-n-propoxyphenoxy)ethyl]amine. The content of isopropyl-methyl-[2-(3-n-propoxyphenoxy)ethyl]amine in ethyl acetate is preferably 7–9 ml ethyl acetate per gram of isopropyl-methyl-[2-(3-n-propoxyphenoxy)ethyl]amine. To the assayed solution of isopropyl-methyl-[2-(3-n-propoxyphenoxytethyl]amine in ethyl acetate, methanol and a solution of phosphoric acid in methanol are added. The amount of phosphoric acid should be around 0.9 to 1.0 molar equivalents, preferably 0.95 equivalents. The total amount of methanol added to the assayed solution should be adjusted to the amount of phosphoric acid used. The concentration of phosphoric acid in the resulting solution of isopropyl-methyl-[2-(3-n-propoxyphenoxy)ethyl]amine in metanol/ethyl acetate should be around 5–15%, by volume, preferably 9–11%, by volume. The precipitated salt is collected, for example by filtration or centrifugation, and thereafter washed with ethyl acetate.

The monophosphate salt of isopropyl-methyl-[2-(3-n-propoxyphenoxy)ethyl]amine can thereafter be further processed by processes known in the art, e.g. converted back to its basic form, i.e. isopropyl-methyl-[2-(3-n-propoxyphenoxy)ethyl]amine, by treatment of aqueous base.

MEDICAL AND PHARMACEUTICAL USE

The monophosphate salt of isopropyl-methyl-[2-(3-n-propoxyphenoxy)ethyl]amine is useful because it possesses pharmacological activity and especially for the use as an anaesthetic compound. It is therefore indicated as a pharmaceutical, especially in the treatment of pain, including localised pain.

According to a further aspect of the invention there is thus provided the monophosphate salt of isopropyl-methyl-[2-(3-n-propoxyphenoxy)ethyl]amine for use as a pharmaceutical, especially in the treatment of pain.

PHARMACEUTICAL FORMULATIONS

The monophosphate salt of isopropyl-methyl-[2-(3-n-propoxyphenoxy)ethyl]amine will normally be administered parenterally, especially injected in the form of pharmaceutical formulations comprising the active ingredient in a pharmaceutically acceptable dosage form. Compositions comprising the monophosphate salt of isopropyl-methyl-[2-(3-n-propoxyphenoxy)ethyl]amine for parenteral administration may include other ingredients commonly used in the parenteral administration of pharmaceutically-active compounds.

According to a further aspect of the invention there is thus provided a pharmaceutical formulation containing the monophosphate salt of isopropyl-methyl-[2-(3-n-propoxyphenoxy)ethyl]amine in admixture with a pharmaceutically acceptable adjuvant, diluent or carrier. Formulations including the monophosphate salt of isopropyl-methyl-[2-(3-n-propoxyphenoxy)ethyl]amine may be prepared by techniques which are known per se. Usually the active substance will constitute between 0.5 and 10% by weight of the preparation, more specifically between 1 and 5% by weight.

According to a further aspect of the present invention, there is provided a method for treatment of a pain which method comprises administration of a therapeutically effective amount of the monophosphate salt of isopropyl-methyl-[2-(3-n-propoxyphenoxy)ethyl]amine to a person suffering from, or susceptible to pain.

The present invention is described in more detail in the following non-limiting examples

EXAMPLES

Example 1

Preparation of the monophosphate salt of isopropyl-methyl-[2-(3-n-propoxyphenoxy)ethyl]amine To an assayed solution of isopropyl-methyl-[2-(3-n-propoxyphenoxy)ethyl]amine (19.0 kg, 75.7 mol) in ethyl acetate (8 ml EtOAc/g isopropyl-methyl-[2-(3-n-propoxyphenoxy)ethyl]amine) is added MeOH (9.6 L) followed by $H_3PO_4$ (4.85 L, 72.5 mol) dissolved in MeOH (19.2 L) over 3 hours at ambient temperature. The resulting slurry of the title compound is then isolated by filtration and the solid material is washed with EtOAc. Yield 89% (41.8 kg wet compound, corresponds to 67.6 mol dry compound); Mp: 131–134° C.

What is claimed is:

1. A phosphate salt of isopropyl-methyl-[2-(3-n-propoxyphenoxy)ethyl]amine.

2. A monophosphate salt of isopropyl-methyl-[2-(3-n-propoxyphenoxy)ethyl]amine.

3. A process for the preparation of the monophosphate salt of isopropyl-methyl-[2-(3-n-propoxyphenoxy)ethyl]amine comprising the following steps:

i) adding phosphoric acid to a solution of isopropyl-methyl-[2-(3-n-propoxyphenoxy)ethyl]amine in an organic solvent system;

ii) allowing the solution to crystallize; and iii) isolating the monophosphate salt of isopropyl-methyl-[2-(3-n-propoxy phenoxy)ethyl]amine thus obtained.

4. A process according to claim 3, characterized in that the organic solvent system used in step i) is ethyl acetate.

5. A process according to claim 3, characterized in that the phosphoric acid added in step i) is added as an alcoholic solution of phosphoric acid.

6. A process according to claim 5, characterized in that the alcoholic solution is a methanolic solution.

7. A process according to claim 3, characterized in that 0.9–1.0 equivalents of phosphoric acid is used in step i.

8. A process according to claim 3, characterized in that 0.95 equivalents of phosphoric acid is used in step i.

9. A process according to claim 3, characterized in that the concentration of phosphoric acid in the resultant solution after complete addition is between 5–15%, by weight.

10. A process according to claim 3, characterized in that the concentration of phosphoric acid in the resultant solution after addition is between 9–11%, by weight.

11. A pharmaceutical formulation comprising the monophosphate salt of isopropyl-methyl[2-(3-n-propoxyphenoxy)ethyl]amine and a pharmaceutically acceptable carrier or diluent.

12. The phosphate salt of isopropyl-methyl-[2-(3-n-propoxyphenoxy)ethyl]amine prepared by the process of anyone of claims 3–10.

13. A method of treatment for the pain which comprises the administration of a therapeutically effective amount of the monophosphate salt of isopropyl-methyl-[2-(3-n-propoxyphenoxy)ethyl]amine to a patient suffering from pain.

14. The pharmaceutical formulation of claim 12, wherein said formulation is suitable for parenteral administration.

15. The pharmaceutical formulation of either claim 12 or 14, wherein said monophosphate salt of an isopropyl-methyl-[2-(3-n-propoxyphenoxy)ethyl]amine comprises between 0.5 and 10% by weight of the preparation.

16. The pharmaceutical formulation of claim 15, wherein said monophosphate salt of an isopropyl-methyl-[2-(3-n-propoxyphenoxy)ethyl]amine comprises between 1 to 5% by weight of the preparation.

17. The method of claim 12, wherein said monophosphate salt of an isopropyl-methyl-[2-(3-n-propoxyphenoxy)ethyl] amine is administered parenterally.

* * * * *